United States Patent
Hotrum et al.

(10) Patent No.: US 9,056,056 B2
(45) Date of Patent: Jun. 16, 2015

(54) PROCESSING FOR DISPERSING AMINO ACIDS

(71) Applicant: N.V. Nutricia, Zoetermeer (NL)

(72) Inventors: Natalie Elizabeth Hotrum, Bennekom (NL); Carla Angèle Paula Buijsse, Wageningen (NL); Robert Johan Joseph Hageman, Wageningen (NL); Adrianus Lambertus Bertholdus Van Helvoort, Wageningen (NL)

(73) Assignee: N.V. NUTRICIA, Zoetermeer (NL)

( * ) Notice: Subject to any disclaimer, the term of this patent is extended or adjusted under 35 U.S.C. 154(b) by 43 days.

(21) Appl. No.: 14/038,342

(22) Filed: Sep. 26, 2013

(65) Prior Publication Data

US 2014/0099344 A1    Apr. 10, 2014

Related U.S. Application Data

(63) Continuation of application No. 12/596,719, filed as application No. PCT/NL2008/050231 on Apr. 21, 2008, now Pat. No. 8,632,817.

(30) Foreign Application Priority Data

Apr. 20, 2007 (WO) ............... PCT/NL2007/050171

(51) Int. Cl.
*A61K 9/50* (2006.01)
*A23J 7/00* (2006.01)
*A23L 1/00* (2006.01)
*A23L 1/305* (2006.01)

(52) U.S. Cl.
CPC ... *A61K 9/50* (2013.01); *A23J 7/00* (2013.01); *A23L 1/0032* (2013.01); *A23L 1/3051* (2013.01); *A23L 1/3053* (2013.01); *A23V 2002/00* (2013.01)

(58) Field of Classification Search
None
See application file for complete search history.

(56) References Cited

U.S. PATENT DOCUMENTS 6,586,008 B1 * 7/2003 Batycky et al. ............ 424/489
2005/0220978 A1 * 10/2005 Arudi et al. ................ 426/656

FOREIGN PATENT DOCUMENTS

| EP | 0252374 A1 | 1/1988 |
| WO | 0193837 A2 | 12/2001 |
| WO | 02065849 A1 | 8/2002 |
| WO | 2005048731 A2 | 6/2005 |
| WO | 2006124870 A1 | 11/2006 |
| WO | 2005096835 A1 | 10/2009 |

OTHER PUBLICATIONS

Kuiken, K. and Lyman, C., "Essential Amino Acid Composition of Soy Bean Meals Prepared from Twenty Strains of Soy Beans," retrieved from http://www.jbc.org.content/177/1/29/full.pdf), as accessed Oct. 22, 2011.*
The Soy Connection, retrieved from <http://soyconnection.com/health_nutrition/technical_info/protein_content.php>, as accessed Oct. 22, 2011.*
Russell Lab, retrieved from: http://www.russelllab.org/aaas/hydrophobic.html, as accessed Oct. 22, 2011.*

* cited by examiner

*Primary Examiner* — David J Blanchard
*Assistant Examiner* — Daniel F Coughlin
(74) *Attorney, Agent, or Firm* — Browdy and Neimark, PLLC

(57) ABSTRACT

A coated proteinaceous material can be produced by contacting the proteinaceous material with de-oiled phospholipids or mixtures thereof containing less than 20% triglycerides. The coating has between 0.1 and 1.5% by weight of the total proteinaceous material, of de-oiled lecithin. The proteinaceous material is hydrophobic, especially amino acids having a hydrophobicity of higher than 1.0 kJ/mol. In particular, the amino acids are leucine, isoleucine, valine, phenylalanine, tryptophan and/or methionine. The coated amino acids can be incorporated into food products and medicaments.

24 Claims, 2 Drawing Sheets

PROCESSING FOR DISPERSING AMINO ACIDS

FIELD OF THE INVENTION

The invention relates to a process for coating amino acids and peptides and for producing dispersible amino acid and peptide preparations. The invention also pertains to the coated material thus produced and to nutritional products containing the coated material.

BACKGROUND

Nutritional compositions destined for feeding patients suffering from certain deficits or diseases often need to be fortified with specific amino acids or peptides. For example, leucine is an important ingredient for compositions intended for replenishing muscular tissue, see e.g., WO01/58284. GB-A-2,292,522 discloses a preparation for supporting the immune system containing, inter alia, methionine, valine, leucine, threonine, phenylalanine, lysine, isoleucine and tryptophan. WO2004/103383 discloses the use of leucine and glycine for the treatment of chronic wounds.

However, some amino acids have insufficient solubility, wettability, sinkability or dispersibility or a bad taste or a combination thereof. This applies especially to large neutral (hydrophobic) amino acids such as leucine, isoleucine, valine, phenylalanine, and tryptophan, and to the sulphur amino acids methionine and cysteine (or cystine). As a consequence, the production of such compositions is hampered with dissolution problems, and the compositions are poorly accepted because of their bad taste.

Prior art methods developed for overcoming this problem include encapsulation of the amino acids, e.g., using oils or other relatively hydrophobic materials, optionally combined with lecithins.

JP-A 2-042967 describes coating of amino acids or drugs with an ethanol or acetone solution of glycerol acetate or lecithin as a surfactant, followed by an oil and again the surfactant. U.S. Pat. No. 6,506,422 discloses a nutritional formula for PKU patients containing casein glycomacropeptide as protein source together with free amino acids including Tyr. The amino acids may be encapsulated with edible fats, such as hydrogenated palm oil. EP-A 363,879 suggests to mask the taste of free amino acids by combining them with candied fruit and a gelling agent such as starch or gums. US2004/0148013 teaches to coat food material, such as amino acids, with an organic zinc salt and a high-melting fat. EP-A 388,237 discloses a coating for amino acids containing about 55% sugar, about 40% hardened fat and about 0.6% lecithin.

SUMMARY OF THE INVENTION

The invention provides an improved approach of producing amino acid preparations of hydrophobic amino acids or peptides, resulting in a better dispersibility of the amino acids and peptides, and in a better acceptability of the resulting food products. The low proportion of triglycerides allows a more effective wetting and dissolution of the particles. The increased dispersibility and concomitant effects also allow a reduction of losses of valuable material during processing.

The invention thus pertains to a process of increasing the dispersibility and/or wettability and/or decreasing the stickability of proteinaceous material by coating particles thereof with a phospholipids composition having a low content of hydrophobic substances such as triglycerides.

The present invention also pertains to coated proteinaceous material which can be obtained using the process of the invention.

Furthermore, the invention concerns a process of producing nutritional compositions containing added proteinaceous material, especially amino acids, in which the coated amino acids or proteins are combined with other food components, including e.g., lipids, carbohydrates, proteins, vitamins, minerals, and optionally further active components. Also, the invention relates to nutritional products containing the coated amino acids or proteins.

DETAILED DESCRIPTION OF THE INVENTION

Figure 1:
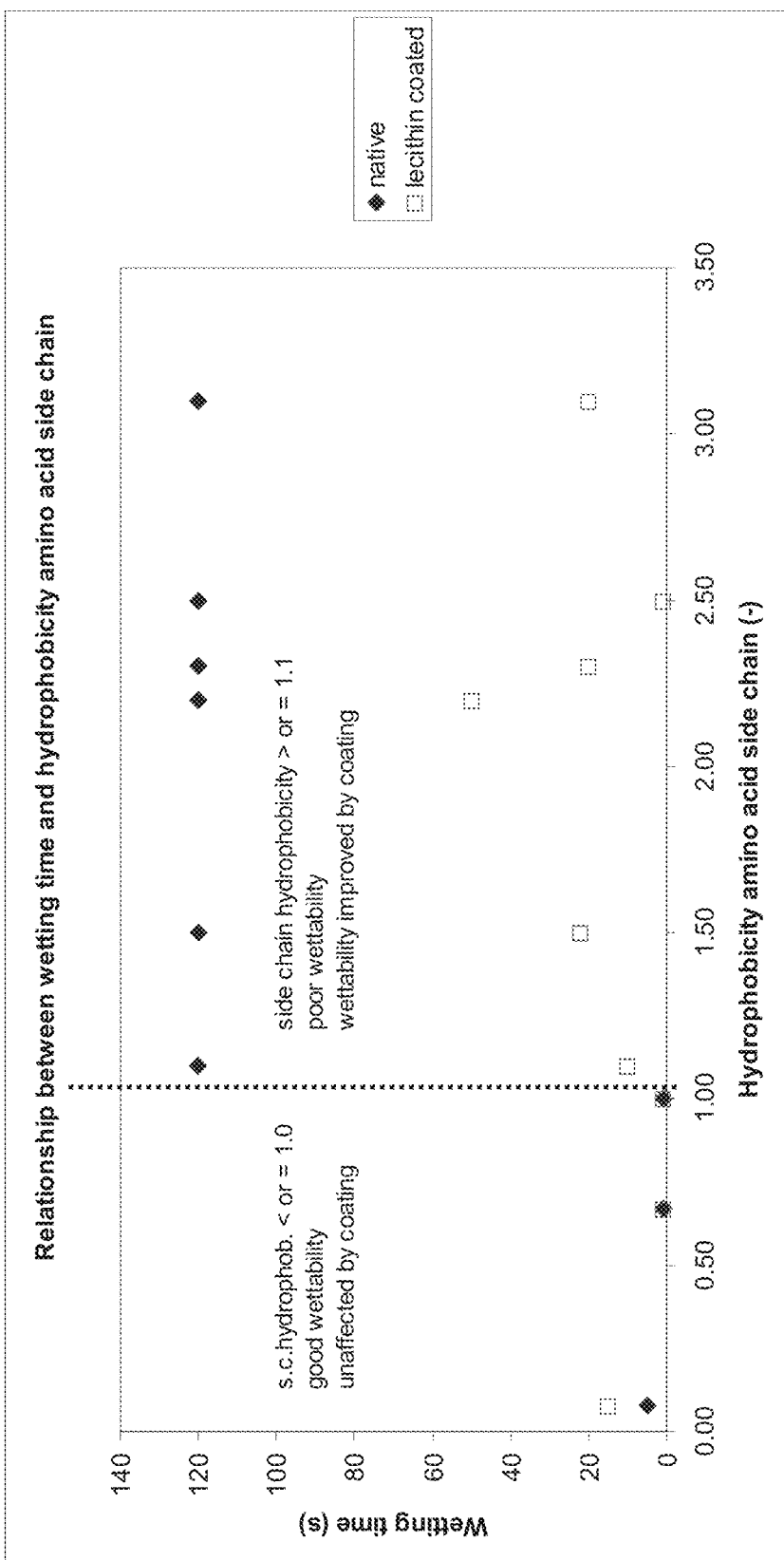
FIG. 1 is a graph showing the relationship between wetting time and hydrophobicity of the amino acid side chain of the coated amino acid. Coating of hydrophilic amino acids (part of the graph left of the dashed vertical line) has minimal or no effects whereas coating of hydrophobic amino acids (right of the dashed line) drastically reduces the wetting time.

The process according to the invention for producing coated particles of hydrophobic proteinaceous material, is characterised by contacting the proteinaceous material with a de-oiled phospholipid composition. Preferred embodiments of the processes and products of the invention are summarized in the appending claims and are further detailed below.

Proteinaceous Material

In the present description "proteinaceous material" is understood as any proteins, peptides, amino acids, and amino acid esters, which may further contain minor amounts (e.g., less than 25 wt. %, preferably less than 5 wt. %) of other material, such as glycosylated proteins, lipoproteins such as proteins conjugated with palmitic or myristic acid, carbohydrates and the like. Such other material is counted as proteinaceous matter for the proteinaceous part only. Preferably, the proteinaceous material comprises at least 80 wt. %, preferably at least 90 wt. % of free amino acids, and/or of peptides having a chain length of no more than 10 amino acid residues, i.e. less than 20 wt. % preferably less than 10 wt. % of peptides and proteins of more than 10 amino acid residues. More preferably, it comprises at least 60 wt. %, especially at least 80 wt. %, more especially at least 95 wt. %, most preferably at least 98 wt. % of the sum of free amino acids and dipeptides. In a particular embodiment, the proteinaceous comprises at least 50 wt. %, preferably at least 75 wt. %, more preferably at least 95 wt. % of free amino acids. Especially it consists essentially of free amino acids only. It is preferred that the proteinaceous material has a crystalline form before coating.

Herein, "free amino acids" mean the amino acids as such, or their salts or esters, or their N-acylated or N-methylated derivatives, such as N-acetylcysteine or N,N-dimethylglycine. Preferably the free amino acids are used as such or as their salts.

The amino acids are in particular hydrophobic amino acids, i.e. amino acids which according to the classification of Eisenburg et al. (*Faraday Symp. Chem. Soc.* 17:109-120 (1982)) have a side chain hydrophobicity (SCH) having a positive value. The side chain hydrophobicity according to Eisenburg et al. is presented in the table below. The values are in kJ/mol.

TABLE

| Hydrophobicity of amino acids in kJ/mol | | | | | | | | | |
|---|---|---|---|---|---|---|---|---|---|
| Arg | Lys | Asp | Gln | Asn | Glu | His | Ser | Thr | Pro |
| −7.5 | −4.6 | −3.0 | −2.9 | −2.7 | −2.6 | −1.7 | −1.1 | −0.75 | −0.29 |
| Tyr | Cys | Gly | Ala | Met | Trp | Leu | Val | Phe | Ile |
| +0.08 | +0.17 | +0.67 | +1.0 | +1.1 | +1.5 | +2.2 | +2.3 | +2.5 | +3.1 |

Especially suitable for use in the present invention are hydrophobic amino acids having a SCH of above 1.0, i.e. Met, Trp, Leu, Val, Phe and Ile. These have a wetting time of more than 120 s, which makes dissolution or dispersion into other food components especially difficult. The wettability (wetting time) can be determined using the method of International IDF Standard 87:1979.

Thus, the proteinaceous material which is coated according to the invention preferably has a hydrophobicity of higher than 1.0 kJ/mol. This means that the (number) average SCH of all amino acids present as such or in dipeptides, or—if present—higher peptides, is 1.0. More preferably, the average SCH is at least 1.2. In particular, the proteinaceous material comprises at least 25 wt. %, on total protein basis, of amino acids selected from Met, Trp, Phe, Leu, Ile and Val, and/or peptides containing at least 50% by number of said amino acids. Alternatively or in addition, preferably at least 50%, especially at least 60%, of all amino acids present in the proteinaceous material are amino acids have an SCH of at higher than 1.0, and/or at least 40%, especially at least 50%, of all amino acids present in the proteinaceous material are amino acids have an SCH of at higher than 2.0

FIG. 1 illustrates the dramatic effect of the coating method of the invention on the wettability of amino acids. The results with Tyr, Gly and Ala (left-hand part of the figure) show that sufficiently hydrophilic amino acids have a short wetting time, and that coating has no or only a minor effect on the wetting time, and the results with Met, Trp, Leu, Val, Phe and Ile (right-hand part of the figure) show that coating of these hydrophobic amino acids drastically reduces the wetting time, from about 120 s to below 50 s.

In addition to the amino acids as listed in the table, other hydrophobic amino acids, such as methylglycine or dimethylglycine can be coated successfully by the process of the invention as well. Peptides to be coated using the process of the invention are those which consist for at least ⅔ of the number of amino acid residues of amino acid having a positive value of their SCH, especially an SCH above 1.0.

The proteinaceous material that is to be coated can be a single component, e.g., a single crystalline hydrophobic amino acid. It can also be a mixture of such components. Furthermore, a mixture of such hydrophobic components and more polar components can be coated according the invention, in particular, a mixture of between 50 and 90 wt. % of hydrophobic amino acids, and between 50 and 10 wt. % of one of more carbohydrates, such as glucose, galactose, lactose, sucrose, maltose or maltodextrins, more preferably non-reducing carbohydrates such as sucrose or trehalose. In another embodiment, it is preferred to coat the hydrophobic proteinaceous components in the substantial absence of polar components, which is defined to be less than 10% polar components.

Phospholipid Composition

A "phospholipid composition" as used herein is any composition containing a substantial proportion of phospholipids as defined below, e.g., at least 40 wt. % or in particular at least 50 wt. %. The phospholipid composition may further contain lipids other than phospholipids, including e.g., triglycerides, diglycerides, monoglycerides, fatty acids and glycolipids, carbohydrates and water. However, where weight percentages are given, these are given on a dry basis, i.e. in the assumed absence of water. A practical example of a phospholipid composition is lecithin. The neutral lipids (triglycerides etc.) and water are usually part of the acetone-soluble fraction of lecithins, whereas the polar lipids (phospholipids, glycolipids) are usually acetone-insoluble. The phospholipids composition is preferably used as a dispersion in water.

A "de-oiled phospholipid composition" is a phospholipid composition having a reduced proportion of lipids, in particular triglycerides. Preferably, the content of neutral lipids, i.e. triglycerides, diglycerides, monoglycerides and fatty acids, of the de-oiled phospholipid composition is less than 30 wt. %, more preferably less than 20 wt. %, most preferably less than 10 wt. %. The triglyceride content is preferably less than 20 wt. %, more preferably less than 10 wt. %, most preferably less than 5 wt. % of the de-oiled phospholipid composition. The phospholipid compositions may also contain carbohydrates, but preferably no more than 20 wt. %, in particular between 2 and 10 wt. %, of the de-oiled phospholipids composition. Furthermore, the phospholipid composition may contain glycolipids as defined below, e.g., between 1 and 50%, especially between 5 and 35 wt. % of the total de-oiled phospholipid composition. The content of phospholipids in the de-oiled phospholipid composition to be used in the invention is preferably at least 65 wt. %, more preferably at least 75 wt. %, most preferably at least 80 wt. % of the de-oiled phospholipid composition. The proportion of phospholipids may also be lower, e.g., at least 45 wt. % or especially between 55 and 75 wt. %, if the composition also contains glycolipids as defined below; in that case, the total proportion of phospholipids and glycolipids taken together is preferably between 70 and 98 wt. %, more preferably between 80 and 95 wt. %.

When disregarding any carbohydrates that may be present, the de-oiled phospholipids composition preferably contains at least 68 wt. % of phospholipids, more preferably at least 78 wt. % phospholipids, if no glycolipids are present. In the alternative, the total proportion of phospholipids and glycolipids taken together—disregarding any carbohydrates—is preferably between 73 and 99 wt. %, more preferably between 83 and 96 wt. %. In the latter case, the content of glycolipids may be between 1 and 52, in particular between 5 and 37 wt. % of the de-oiled phospholipids composition (phospholipids, glycolipids and neural lipids). The triglyceride content is preferably below 20 wt. %, more preferably below 10 wt. %, especially below 5 wt. %, and the combined neutral lipid content below, 31, preferably below 20 and more preferably below 10 wt. % respectively.

For the purpose of the invention, a "phospholipid" is any compound having a phosphate group and at least one long-chain hydrocarbon group, in particular a fatty acid residue (long-chain meaning at least 15 carbon atoms). In particular, a phospholipid contains one or two long-chain hydrocarbon groups on one side of the phosphate group, usually with an interconnecting glyceryl group, and optionally a polar group at another side of the phosphate group. The phospholipids preferably comprise one or more of phosphatidylcholine (PC), phosphatidylethanolamine (PE), phosphatidylserine (PS), phosphatidylinositol (PI), optionally phosphatidic acid (PA), phytoglycolipids and phosphosphingolipids including sphingomyelin, i.e. phospholipids in which the diglyceride residue has been replaced by a ceramide unit, and which have a choline group, an inositol or other sugar residue or other polar group on the phosphate group. Also suitable are lysophospholipids (hydrolysed phospholipids), i.e. phospholipids having only one long-chain fatty acid residue per molecule. The phospholipids may be a single component, e.g., phosphatidylcholine, or, more commonly, a mixture of components.

A "glycolipid", which may be present in the (de-oiled) phospholipid composition, is understood to be a compound containing at least one long-chain hydrocarbon unit and at least one sugar unit which may also be sulphated ("sulpholipid"). Suitable glycolipids include glycosylated ceramides, such as GalCer, GlcCer, LacCer, and the more complex gangliosides, containing a chain of glycosyl residues, one or more which may carry a sialyl group.

The phospholipid composition and de-oiled phospholipid composition to be used for coating the amino acids or peptides and/or proteins can be any food-grade phospholipid composition or lecithin. Suitable phospholipid compositions include soy, sunflower, rapeseed or egg or other lecithin, which have a low content of oil (triglycerides or other hydrophobic material). The oil (neutral lipid) content is preferably less than 20 wt. %, more preferably less than 10 wt. %, most preferably less than 5%, based on the total weight of the de-oiled phospholipid composition (i.e. on the total of phospholipids, glycolipids, carbohydrates and neutral lipids). The oil content can be determined for example as acetone-soluble material. Thus the phospholipid compositions to be used according to the invention preferably have a content of acetone-insoluble material of at least 80 wt. %, preferably at least 90 wt. %, most preferably at least 95 wt. %. Moreover, the phospholipids to be used may be a commercially available de-oiled phospholipids preparation in dry powder, granulated or wax-like form or a dispersion of phospholipids in aqueous media.

The coated proteinaceous material can be characterised by its phosphorus content resulting from the phospholipid coating. Thus, the coated proteinaceous material of the invention has a phosphorus content between 0.001 and 0.1 wt. % (on elemental phosphorus), preferably between 0.005 and 0.05 wt. %.

Process

The process of the invention can be carried out using conventional equipment such as pan coaters, fluid bed coaters and the like. Powder of the amino acids or peptides is then contacted with a dispersion of the lecithin in a suitable solvent. Suitable solvents include water, in which optionally additional components can be dissolved or dispersed. Such additional components include processing aids and buffers, minerals, trace elements, some vitamins, carbohydrates like sucrose or other non-reducing sugars. The concentration of the phospholipids in the solvent should be between e.g., 1 wt. % and the critical micelle concentration, which depends on the further constituents and can be determined in a manner known to the skilled person. Preferably, the phospholipids concentration is below 15 wt. %, especially between 2 and 10 wt. %.

An amount of the dispersion is applied to the final product or amino acids, which results in a good wettability and dispersibility of the final product. The process according the invention can result in a coating or a granulation (when higher amounts of phospholipids are brought on the product). Typically the content of de-oiled lecithin in the final product is between 0.05 and 15 wt. %, preferably between 0.1 and 5 wt. %. The method of application can comprise spraying, dipping etc. The contact temperature is preferably between 20 and 60° C., more preferably between 30 and 50° C., preferably for a period of e.g., 5 to 60 min, more preferably 10 to 45 min. After spraying or other contacting procedure, the particles are preferably dried, e.g., in air for 3-30 min, preferably 6-20 min, at a temperature between 60 and 100° C., preferably between 70 and 90° C. The dried particles are then conditioned and are ready for use in preparing food products.

Nutritional Products

The coated particles can be packed and used as a product which can be dissolved or suspended as such, or in combination with other ingredients, in any food product or drink by the consumer before consumption.

The particles can also be blended with other powdered ingredients, such as non-hydrophobic amino acids, carbohydrates, proteins including milk powder or whey powder, vitamins, minerals etc. to manufacture a premix. Such a premix can be packed and used by consumers for preparing a ready to use food product or drink. The premix can also be used for producing solutions or dispersions on a commercial scale, which can be used in the manufacture of ready to use liquids or of slurries which can be spray-dried. Processes for manufacturing ready to use liquids are known in the art and may include new mixing steps with other ingredients, homogenisation and heat treatment steps. Methods for spray-drying liquids are also known in the art.

The coated particles are readily dispersible and wettable and are very stable during storage at room temperature, normal moisture content in the dark and under conventional atmosphere. They have and improved sinkability (resistance to floating on or settling from the dispersion). This stability can be further improved by applying methods known in the art, such as packaging under nitrogen and decreasing atmospheric humidity.

The coated amino acids are particularly suitable for fortification of clinical nutrition, which are complex products. Hence, the invention also pertains to nutritional compositions, containing carbohydrates, proteins, vitamins, and/or minerals, and further containing between 0.1 and 50% by weight, preferably between 0.5 and 40%, more preferably between 2.5 and 25% by weight, of the total of carbohydrates, protein (total proteinaceous material) and lipids, of a coated proteinaceous material as described above. It is preferred that the composition contains at least carbohydrates, preferably at least 10% of the caloric content of the composition, especially between 25 and 70% of the caloric content. If the coated proteinaceous material only contains one or a few amino acids, it will often be preferred that further protein material is present. The total protein (including amino acids) is preferably at least 5% of the caloric content of the composition, more preferably between 10 and 40% of the caloric content. The presence of lipids is also possible, in particular between 5 and 35% of the caloric content, although the lipid content will often be low, or zero. The composition may be a liquid composition, although a dry composition is often preferred. A powdered product constitutes a preferred embodiment of the invention.

The coated particles and the products containing them can be used as a medicinal or health food or as a supplement, especially for treating conditions which require the administration of elemental protein compositions (comprising free amino acids or small peptides rather than intact proteins), or which require supplementation of specific amino acids. Where more than one amino acid is to be incorporated in the food product or supplement, at least one, hydrophobic, amino acid is included in the coated form according to the invention. Other amino acids, especially non-hydrophobic ones, may be added as such, or with a conventional coating, for example using carbohydrates. Alternatively, all amino acids can be combined before coating, and then be coated according to the invention.

As a example, a supplement for phenylketonuria (PKU) patients containing a mixture of amino acids, preferably all amino acids with the exception of phenylalanine. At least one of the hydrophobic amino acids, but preferably all of Ile, Leu, Val, Trp and Met, are incorporated with a de-oiled lecithin coating, while other amino acids are added as such. Alternatively, all amino acids (except Phe) are coated by the process of the invention and then incorporated into the supplement.

EXAMPLES

Example 1

Amino Acid with Improved Dispersibility for Use as Raw Material

A de-oiled soy lecithin obtained from Cargill Texturizing Solutions containing acetone-insoluble material of more than 96%, was dispersed in water until a final concentration of 5.9 wt. %. An amount of 50 kg 99% pure leucine powder obtained from Rexim was placed in a fluid bed agglomerator, Aeromatic AG obtained from Niro Inc. Fluidisation was started at a bed temperature of 34° C. and the lecithin dispersion was sprayed for 30 min at a rate of 0.143 l/min. The powder was then dried by passing heated air (70°) for 10 min. and subsequently cooled to 26° C. Then the agglomerator was stopped, the powder was sieved using a sieve of 2000 μm mesh and filled in bags.

Figure 2:
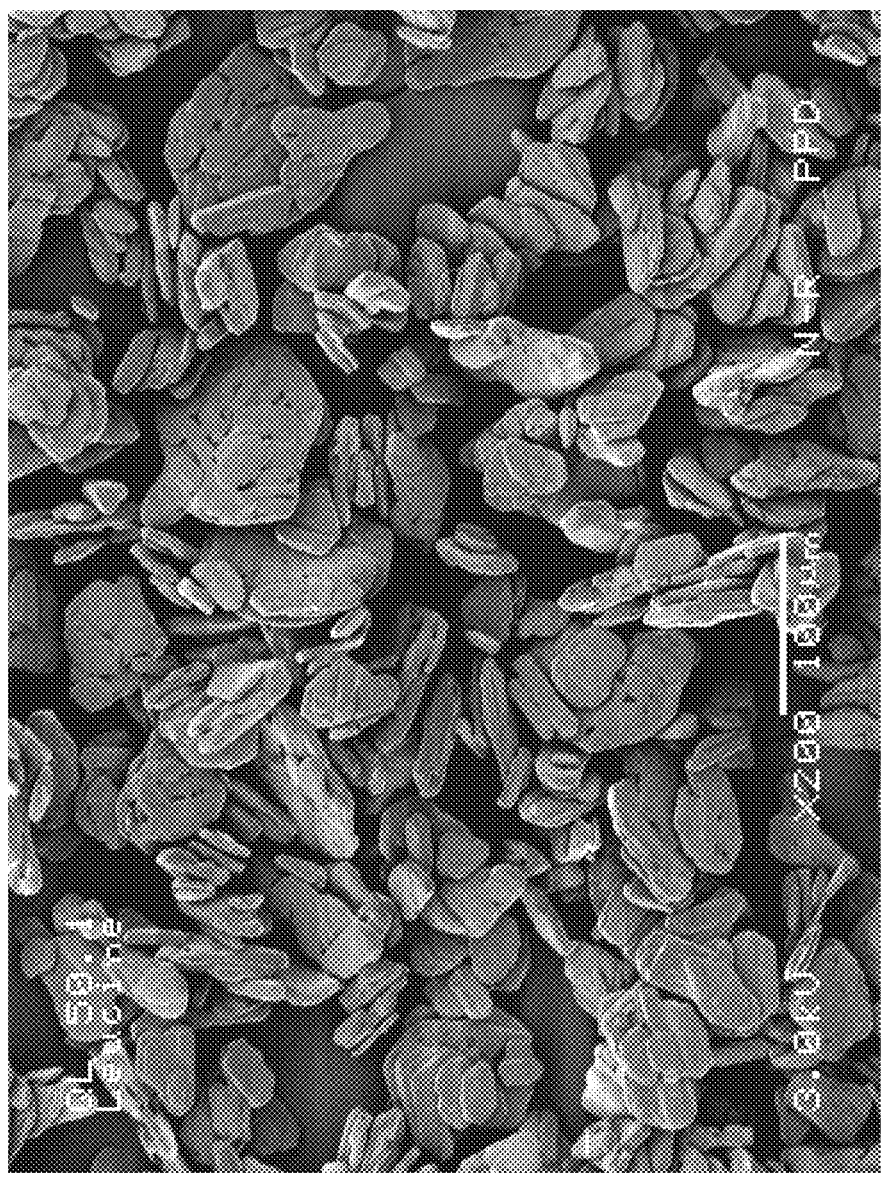
FIG. 2 is an electron micrograph of leucine powder coated by the method of the invention.

FIG. 2 shows an electron microscopy image (×200) of leucine powder coated according to the present example. The wetting times was >120 s. The powder had a good dispersibility in water determined according to the method of International IDF Standard 87:1979.

Example 2

Dry-blended Powder for Treatment of Children with a Metabolic Disorder

A powder supplement was prepared for the dietary management of phenylketonuria and hyperphenylalaninemia. The supplement is not nutritionally complete. It contains per 100 g:

| | |
|---|---|
| Energy | 1189 kJ (280 kcal) |
| Amino acids | 71.9 g |
| (a) hydrophobic amino acids excluding phenylalanine (lecithin-coated using process of Example 1) | 18.6 g |
| (b) non-hydrophobic amino acids | 53.3 g |
| Lipids | 0.14 g |
| De-oiled lecithin | 0.14 g |
| Carbohydrates | 10 g |
| Minerals | |
| Na | 540 mg |
| K | 1200 mg |
| Ca | 2300 mg |
| Mg | 300 mg |
| P | 1380 mg |
| Cl | 900 mg |
| Fe | 30 mg |
| Trace elements | |
| Zn | 30 mg |
| Cu | 2.1 mg |
| I | 340 μg |
| Mn | 3.6 mg |
| Cr | 120 μg |
| F | 1.8 mg |
| Mo | 95 μg |
| Se | 50 μg |
| Vitamins | |
| Vitamin A | 1.2 mg |
| Vitamin $D_3$ | 18 μg |
| Vitamin E | 21 mg |
| Vitamin $K_1$ | 57 μg |
| Vitamin $B_1$ | 1.8 mg |
| Vitamin $B_2$ | 2.4 mg |
| Vitamin $B_6$ | 2.7 mg |
| Niacin | 12.6 mg |
| Folic acid | 288 μg |
| Biotin | 90 μg |
| Vitamin $B_{12}$ | 3.6 μg |
| Pantothenic acid | 11.4 mg |
| Vitamin C | 180 mg |
| Choline | 780 mg |
| Myo-inositol | 265 mg |
| Other | |
| Carnitine | 150 mg |

The product was stable and readily dispersible in water of room temperature and had a good taste.

Example 3

Nutritionally Complete Product Enriched with Dry-Blended Amino Acid

A nutritionally complete product was prepared for the treatment of cancer patients at risk of suffering from cachexia. It contains per 100 g:

| | |
|---|---|
| Energy | 1794 kJ (428 kcal) |
| Protein | 27.0 g |
| (a) Milk protein isolate | 19.1 g |
| (b) Whey protein concentrate | 4.94 g |
| (c) Leucine (Example 1) | 2.95 g |
| Lipids [marine oil + vegetable] | 14.2 g |
| (a) EPA | 1.50 g |
| (b) DHA | 0.72 g |
| Carbohydrates | 46.5 g |
| (a) sucrose | 11.2 g |
| (b) maltodextrin | 22.5 g |
| (c) trehalose | 11.2 g |
| (d) lactose | 1.58 g |
| Fiber | 5.4 g |
| (a) Fructosaccharide | 0.53 g |
| (b) GOS | 4.81 g |

The leucine is dry mixed with the powder after spray-drying of an emulsion of the other ingredients. The product was stable and readily dispersible in water of room temperature and had a relatively good taste.

What is claimed is:

1. A coated proteinaceous material comprising at least 60 wt. % of the sum of free amino acids and dipeptides, which material comprises:
    (a) at least 25 wt. %, on a total protein basis, of amino acids selected from the group consisting of Met, Trp, Phe, Leu, Ile, Val, Ala, Gly, Cys and Tyr; and
    (b) a coating comprising between 0.1 and 1.5%, by weight of the total proteinaceous material, of a de-oiled phospholipid composition.

2. The coated proteinaceous material according to claim 1, comprising between 0.001 wt. % and 0.1 wt. % phosphorus.

3. The coated proteinaceous material according to claim 1, wherein the amino acids of (a) are selected from the group consisting of Met, Trp, Phe, Leu, Ile and Val.

4. The coated proteinaceous material according to claim 1, in which the proteinaceous material comprises at least 50 wt. %, on a total protein basis, of said amino acids.

5. The coated proteinaceous material according to claim 1, in which the proteinaceous material comprises at least 75 wt. %, on a total protein basis, of free amino acids or their salts.

6. The coated proteinaceous material according to claim 1 wherein the de-oiled phospholipid composition contains less than 20 wt. % triglycerides as a percentage of dry weight.

7. The coated proteinaceous material according to claim 6, in which said wt % of triglycerides in the de-oiled phospholipid composition is less than 10 wt. %.

8. The coated proteinaceous material according to claim 1, in which the de-oiled phospholipid composition contains at least 65 wt. % of phospholipids.

9. A nutritional composition, comprising:
(i) carbohydrates, proteins, vitamins, and/or minerals, and
(ii) the coated proteinaceous material according to claim 1 at a wt. %, based on the weight of the carbohydrates and proteins, of between 0.1 wt % and 50 wt %.

10. The nutritional composition according to claim 9, wherein the wt % of the coated proteinaceous material is between 0.5 wt. % and 30 wt. %.

11. A nutritional composition, comprising
(i) carbohydrates, proteins, lipids, vitamins, and/or minerals, and
(ii) the coated proteinaceous material according to claim 1 at a wt. %, based on the weight of the carbohydrates, proteins and lipids, of between 0.1 wt % and 50 wt %.

12. The nutritional composition according to claim 11, wherein the wt % of the coated proteinaceous material is between 0.5 wt % and 30 wt. %.

13. A process for producing the coated particles of hydrophobic proteinaceous material of claim 1, comprising contacting said proteinaceous material with a de-oiled phospholipid composition to produce said coated particles.

14. The process according to claim 13 in which the amino acids are selected from the group consisting of Met, Trp, Phe, Leu, Ile and Val.

15. The process according to claim 13, in which the proteinaceous material comprises at least 75 wt. %, on a total protein basis, of free amino acids or their salts.

16. The process according to claim 13 wherein the de-oiled phospholipid composition contains less than 20 wt. % triglycerides as a percentage of dry weight.

17. The process according to claim 16, in which the de-oiled phospholipid composition comprises less than 10 wt. % triglycerides.

18. The process according to claim 13, in which the de-oiled phospholipid composition comprises at least 65 wt. % phospholipids.

19. The process according to claim 13, in which the de-oiled phospholipid composition comprises at least 70 wt. % phospholipids and/or glycolipids.

20. A process for producing a nutritional composition, comprising combining
(i) carbohydrate, protein, vitamin, and/or mineral food components with
(ii) the coated proteinaceous material according to claim 1, thereby producing said nutritional composition.

21. A process for producing a nutritional composition, comprising combining:
(i) carbohydrate, protein, vitamin, and/or mineral food components with
(ii) the coated proteinaceous material according to claim 2, thereby producing said nutritional composition.

22. A nutritional composition, comprising:
(i) carbohydrates, proteins, vitamins, and/or minerals, and
(ii) the coated proteinaceous material according to claim 3 at a wt. %, based on the weight of the carbohydrates and proteins, of between 0.1 wt % and 50 wt %.

23. A process for producing a nutritional composition, comprising combining:
(i) carbohydrate, protein, vitamin, and/or mineral food components with
(ii) the coated proteinaceous material according to claim 3, thereby producing said nutritional composition.

24. A process for producing a nutritional composition, comprising combining:
(i) carbohydrate, protein, vitamin, and/or mineral food components with
(ii) the coated proteinaceous material according to claim 6, thereby producing said nutritional composition.

* * * * *